(12) United States Patent
Piron et al.

(10) Patent No.: US 10,552,959 B2
(45) Date of Patent: Feb. 4, 2020

(54) SYSTEM AND METHOD FOR USING IMAGING QUALITY METRIC RANKING

(71) Applicants: Cameron Anthony Piron, Toronto (CA); Murugathas Yuwaraj, Toronto (CA)

(72) Inventors: Cameron Anthony Piron, Toronto (CA); Murugathas Yuwaraj, Toronto (CA)

( * ) Notice: Subject to any disclaimer, the term of this patent is extended or adjusted under 35 U.S.C. 154(b) by 4 days.

(21) Appl. No.: 15/903,237

(22) Filed: Feb. 23, 2018

(65) Prior Publication Data

US 2019/0266727 A1    Aug. 29, 2019

(51) Int. Cl.
    G06T 7/00     (2017.01)
    A61N 5/10     (2006.01)
    G16H 30/40    (2018.01)
    A61B 5/00     (2006.01)

(52) U.S. Cl.
    CPC .......... *G06T 7/0016* (2013.01); *A61B 5/4848* (2013.01); *A61N 5/1064* (2013.01); *G16H 30/40* (2018.01); *G06T 2207/30168* (2013.01)

(58) Field of Classification Search
    None
    See application file for complete search history.

(56) References Cited

U.S. PATENT DOCUMENTS

| | | | |
|---|---|---|---|
| 2009/0135191 A1* | 5/2009 | Azar | A61B 6/502 345/522 |
| 2010/0284598 A1* | 11/2010 | Zhao | G06T 7/33 382/131 |
| 2015/0093008 A1 | 4/2015 | Kaftan et al. | |
| 2016/0070436 A1* | 3/2016 | Thomas | A61B 5/055 |
| 2017/0103173 A1 | 4/2017 | Vilsmeier et al. | |

FOREIGN PATENT DOCUMENTS

| | | |
|---|---|---|
| GB | 2536274 A | 9/2016 |
| WO | 2012025855 A1 | 3/2012 |
| WO | 2016082017 A1 | 6/2016 |
| WO | 2016097910 A1 | 6/2016 |

OTHER PUBLICATIONS

Search report issued by the Intellectual Property Office of the United Kingdom in relation to corresponding GB Application No. GB1902538.6 dated Aug. 16, 2019, 3 pgs.

\* cited by examiner

*Primary Examiner* — Delomia L Gilliard

(57) ABSTRACT

A method and system is provided for storing and analyzing clinical imaging data. The method includes obtaining patient images from two or more modalities, registering the images, determining position information of a voxel, calculating and assigning a quality metric for the voxel, storing the voxel information and at least one searchable header as imaging data in a computer memory, and modifying or maintaining treatment based on the imaging data. The system includes a memory and a processor, the processor configured to obtain images from two or more modalities, register and store the image set in memory, calculate a quality metric for a voxel in the image set, store the voxel quality metric with the image set in the memory, and modify or maintain treatment based on the calculated qualitative metric.

11 Claims, 2 Drawing Sheets

SYSTEM AND METHOD FOR USING IMAGING QUALITY METRIC RANKING

FIELD

The present disclosure relates to medical imaging and more specifically to medical imaging in patient treatment.

BACKGROUND

Medical records of a patient often include imaging data, such as Magnetic Resonance Imaging (MM), X-ray, ultrasound (US), and Computed Tomography (CT) images. The medical images are typically obtained in connection with a trauma or disease diagnosis, and may include multiple related medical images taken at different stages of the patient's treatment. The multiple images can also include multiple imaging modalities, i.e. the images are obtained using different imaging technologies.

It is advantageous to have as much of a patient's image data as possible available to a practitioner, for assessing the patient. Institutes such as hospitals incorporate computer-implemented systems to store and provide image data to practitioners. An example of a commonly used system is PACS (picture archiving and communication system). PACS is a healthcare technology that captures and stores medical images from multiple modalities, and allows retrieval and viewing of the images. One problem with PACS is the lack of interoperability of different PACS systems, for example a PACS deployed by an emergency unit of a hospital may not communicate with PACS deployed by the radiology or pathology unit of the same hospital, and different health institutes may deploy PACS that are non-interoperable. Thus, the image data collected by one health unit is not easily accessed by another health unit. A PACS also requires a medical professional, such as a radiologist, to review and interpret the image data and create a structured report. Further, there is no quality control on the images stored in a PACS.

In assessing outcomes, such as a patient status, medical treatment effectiveness, health institute success and medical practitioner performance, it would be ideal to have all medical images related to a patient accessible from a single access point, and to be able to ascertain the reliability of the medical image data.

SUMMARY

An object of the present disclosure is to provide a system and method for integrating patient image data and calculating quality metrics for the integrated image data.

Thus by one broad aspect of the present invention, a computer-implemented method to store and analyze clinical imaging data for a treatment program is provided, comprising obtaining two or more images of a patient from two or more modalities, registering the images to provide a multimodal image set, determining a position information of a voxel in the multimodal image set, calculating a quality metric for the voxel of the multimodal image set, assigning the quality metric to the voxel, storing the voxel, the voxel position information, the quality metric and at least one searchable header as imaging data in a memory of a computing device, and modifying or maintaining the treatment program based on the imaging data.

By another broad aspect of the present invention, a system for storing and analyzing clinical imaging data for a treatment program is provided, comprising a memory and a processor interconnected with the memory, the processor configured to obtain two or more images from two or more modalities, store the images in the memory, register the images to provide a multimodal image set, store the multimodal image set in the memory, calculate a quality metric for a voxel in the multimodal image set, store the voxel quality metric with the multimodal image set in the memory, and modify or maintain the treatment program based on the calculated qualitative metric.

BRIEF DESCRIPTION OF THE DRAWINGS

The foregoing and additional aspects and embodiments of the present disclosure will be apparent to those of ordinary skill in the art in view of the detailed description with reference to the following figures, in which.

DETAILED DESCRIPTION

Figure 1:
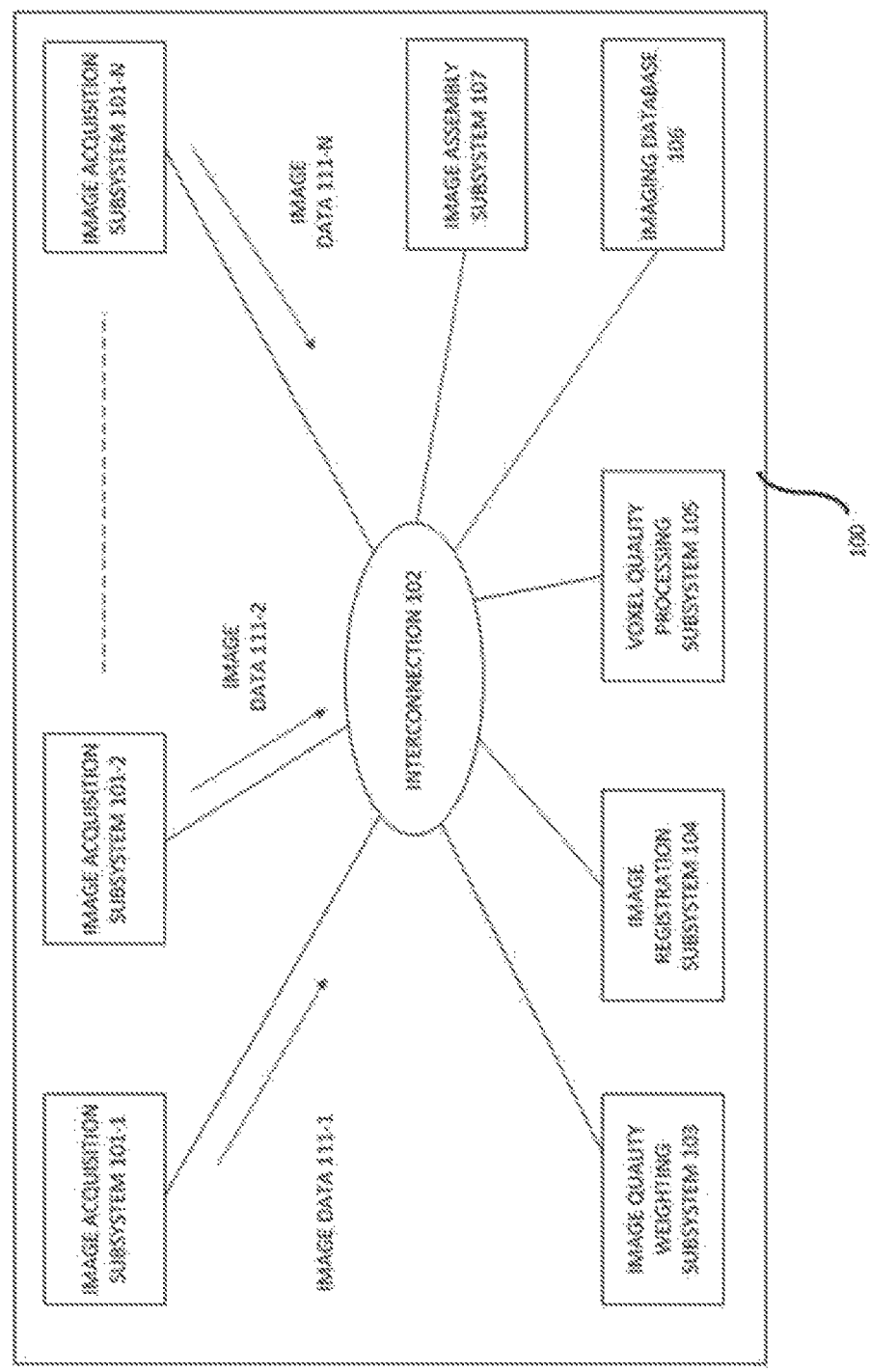
FIG. 1 illustrates an embodiment of a system to calculate a voxel and image quality metric as disclosed herein.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 25 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the term "quantitative state" means a quantitative measurement of a patient status.

As used herein, the term "quantitative registration" means registration of images using quantitative data derived from the imaging modality. These quantitative metrics may include T1, T2, cell density, tissue density, tissue anisotropy, tissue stiffness, fluid flow per volume or area, electrical conductivity, pH and pressure.

As used herein, the term "quality metric" means the quality value assigned to an image or a voxel of an image.

Medical practitioners today are increasingly focused on precision medicine and targeted therapy. To meet these needs, it is important for medical practitioners to obtain high quality patient images at the appropriate times. Furthermore, in order for a practitioner to achieve precision and be able to get a holistic view of the progress of a treatment program for a patient, it is necessary to obtain quantitative states which correlate to the progress.

As an example, when a cancer patient is treated, an oncologist may require images from the radiological unit of a medical facility such as a hospital. Furthermore, the oncologist may require these images at different stages of treatment of the patient, such as when:

chemotherapy is performed,
surgery is performed,
radiotherapy is performed, and
laser treatment is performed.

A database of high quality image data is also useful in, for example, determining the order of procedures within a treatment program. In the case of cancer treatment, having a database of high quality image data may be of assistance to an oncologist seeking to determine whether it would be best to begin with chemotherapy or surgery.

A system used in many institutes for image data storage and access is PACS (picture archiving and communication system). PACS is a healthcare technology that captures and stores medical images from multiple modalities, and allows retrieval and viewing of the images. One problem with PACS is the lack of interoperability of different PACS systems, for example a PACS deployed by an emergency unit of a hospital may not communicate with PACS deployed by the radiology or pathology unit of the same hospital, and different health institutes may deploy PACS that are non-interoperable. Thus, the image data collected by one health unit is not easily accessed by another health unit. A PACS also requires a medical professional, such as a radiologist, to review and interpret the image data and create a structured report. Further, there is no quality control on the images stored in a PACS.

As would be known to one having skill in the art, image registration refers to the process of placing two images in a common coordinate system, such that any given set of coordinates in the common system identifies portions of both images depicting the same area, for example, of a patient. An example of an image registration process is provided in PCT/CA2014/000849 "METHOD, SYSTEM AND APPARATUS FOR QUANTITATIVE SURGICAL IMAGE REGISTRATION", filed Nov. 27, 2014, and published on Jun. 2, 2016. Multiple medical images may be registered, i.e. overlaid and aligned, using any of a number of methods. Typically, image registration depends on abstracting the image into features that are common between two (or many) different imaging sets. This includes the detection of edges in the image, by way of edge detection algorithms, or features. Another method is the use of mutual information metrics between at least two different data sets. Often images are made of differing contrasts, however the absolute value of the voxels of the images have no meaning, the information lies in the relative value of the grey-scale or color value of pixels.

Image registration is achieved by first using a baseline set of images (for example, MRI images), then a second set of images is registered using another modality (for example CT, ultrasound, video, optical navigation, etc.). Points on the first set and second set are co-registered based on common elements for example via calibration to a common (X, Y, Z) coordinate or via setting to some baseline position. In one embodiment, registration and co-registration of images is assisted by high-speed computers, processors and artificial intelligence (AI).

U.S. patent application Ser. No. 15/311,833 (Pub. No. US2017/0103173 A1) describes a system for acquiring and using medical image data before and after a medical procedure. The system also performs image registration. Image data and non-image data is collected from a patient pre- and post-operatively, including the patient status and medical condition. The pre-operative data is used to plan a medical procedure and the post-operative data is used to determine a quality of the outcome of the medical procedure. The outcome quality measure is used to further refine medical treatment plans, determine the most cost-efficient treatment, score practitioner performance and score institute performance. Multiple images and multi-modal images from multiple patients are registered to provide an atlas. The atlas can be used for reference when a patient image is obtained. What is lacking in the described system is a measurement of the quality of the images and a quality metric for the registered images, as well as image registration for a given patient to determine a longitudinal assessment of the patient's health.

Another approach for image registration is the integration of actual quantitative information that can be measured in a 3-dimensional space of the object of interest, such as methods described in PCT/CA2014/000849 "METHOD, SYSTEM AND APPARATUS FOR QUANTITATIVE SURGICAL IMAGE REGISTRATION", filed Nov. 27, 2014 and published on Jun. 2, 2016, which is herein incorporated by reference in its entirety. For instance, flow of fluid through vessels can be imaged in a quantitative manner by Doppler-flow using ultrasound and optical coherence tomography (OCT), but this is done at different imaging scales. The actual measure of the flow however is identical, and if calculated through the two modalities, provides a 3D map of an absolute value that is independent of many other factors that tend to introduce artifacts or uncertainty into the registration process. Additionally, MM can measure flow by way of a different phenomenon, phase-contrast imaging, however the absolute value of flow would be the same as what is measured using ultrasound or optical coherence tomography. This allows for two independent measurements of the same information at differing scales. Quantitative measurements offer a highly accurate means to register, and correlate data, in a reliable means across multiple imaging modalities that can be acquired at multiple scales with greater certainty.

What is important for image registration using quantitative information is that the data is acquired in a manner that retains a quantitative physical metric, that the physical scale of the volume of data acquired is maintained and known (warps or scaling issues are corrected), and the location of where that data was acquired is known. When two or more modalities can measure the same imaging metric in a quantitative means, it provides a common point of information transfer (tagging, registration, segmentation). This concept extends to MM, US, OCT, photo-acoustic imaging, CT, X-ray, current density imaging methods, Raman spectroscopy, mass spectroscopy to name a non-limiting list. In many cases, there is no currently determined imaging correlate between the modalities.

An improvement of the systems and method that is the subject of the present disclosure over the works of prior art described above is that multimodal images from the same patient are registered, and quality metrics are determined for the registered images and stored with the images. More specifically, a quality metric is associated with a voxel of registered images. Image quality metrics can provide more accurate conclusions on treatment effectiveness, patient outcome and practitioner performance.

Figure 2:
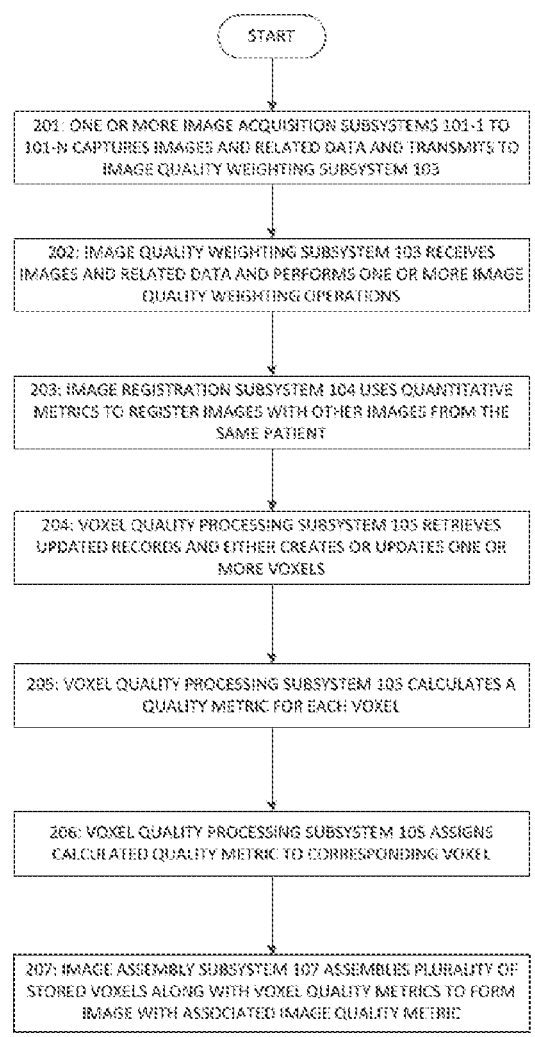
FIG. 2 illustrates an embodiment of a process flow to calculate a voxel and image quality metric as disclosed herein.

FIGS. 1 and 2 show an example embodiment of the system and method that is the subject of the present disclosure. In FIG. 1, system 100 comprises one or more image acquisition subsystems 101-1, 101-2 to 101-N. These image acquisition subsystems are used to capture or acquire medical images and comprise, for example, an optical coherence tomography (OCT) unit, a magnetic resonance imaging (MRI) unit, a Raman spectroscopy unit, a biochemistry imaging unit, a biopsy imaging unit, an X-ray unit, an ultrasound unit and a computerized tomography (CT) scanning unit. Medical images acquired comprise biopsy images, X-rays, ultrasound images, MM images and CT scans.

In step 201 of FIG. 2, one or more of the image acquisition subsystems 101-1, 101-2 to 101-N captures images and other data related to the captured images. Each of the image acquisition subsystems represent a corresponding modality. The data related to the captured images comprises quantitative metrics and metadata such as:

Date of image capture,
Location of image capture, such as a facility name,
Name of person capturing the image, such as a physician,
Level of training of the person collecting the data, which in some embodiments may include a score associated with the person's competency,
Calibration status of the subsystem used to capture the image and the other data,
Last date of calibration of the subsystem used to capture the image and the other data,
Time of image capture,
Treatment corresponding to the captured image, and
Size of captured image file.

Image acquisition subsystems 101-1, 101-2 to 101-N are coupled to the other components of system 100 via interconnection 102 as shown in FIG. 1. Interconnection 102 is constructed using one or more communication technologies known to those of skill in the art. These communication technologies include, for example, a local area network (LAN), a campus area network (CAN), a metropolitan area network (MAN), a fiber optic network, a wireless network, a satellite communication link, a terrestrial communication link, a Bluetooth® communication link or a near field communication (NFC) link. In some embodiments, interconnection 102 is comprised of one or more networks. In some embodiments, interconnection 102 comprises private networks. In other embodiments, interconnection 102 comprises public networks. In some of these embodiments, interconnection 102 comprises a mixture of public and private networks.

In addition, imaging database 106 is coupled to the other components of system 100 via interconnection 102 as shown in FIG. 1. Imaging database 106 comprises records corresponding to patients which include, for example, image data and related data, medical records and other records. In one embodiment, imaging database 106 is coupled to external databases so as to retrieve information from the external databases as necessary. In one embodiment, imaging database 106 further comprises a database server. The database server receives one or more commands from, for example, the other components of system 100 and translates these commands into appropriate database language commands to retrieve and store data into database 106. In one embodiment, imaging database 106 is implemented using one or more database languages known to those of skill in the art, including, for example, Structured Query Language (SQL). In a further embodiment, since imaging database 106 stores data for a plurality of patients, there may be a need to keep the set of data related to each patient separate from the data relating to the other patients. In some embodiments, imaging database 106 is partitioned so that data related to each patient is separate from the other patients. Then, within each partition, different groups of people may have access to different subsets of the data set within the partition. In a further embodiment, when data is entered into imaging database 106, associated metadata is added so as to make it more easily searchable. In a further embodiment, the associated metadata comprises one or more tags. In yet another embodiment, imaging database 106 presents an interface to enable the entering of search queries.

The sizes of captured image files may be in the order of gigabytes (GB) or even terabytes (TB). In one embodiment, as part of step 201 the image acquisition subsystems 101-1 to 101-N perform compression of the captured images so as to reduce storage space requirements and transmission bandwidth requirements.

The one or more image acquisition subsystems 101-1 to 101-N may then transmit captured image data 111-1 to 111-N over interconnection 102 to image quality weighting subsystem 103. Image data 111-1 to 111-N comprises image files which may or may not be compressed, as described above. Additionally, in some embodiments, image data 111-1 to 111-N comprise the metadata related to said images as described above. Each of image data 111-1 to 111-N represents a different modality corresponding to an image acquisition subsystem 101-1 to 101-N.

Image quality weighting subsystem 103 is coupled to the other components of system 100 via interconnection 102 as shown in FIG. 1 In step 202, image quality weighting subsystem 103 receives the image data 111-1 to 111-N and performs one or more image quality weighting operations. Image quality weighting subsystem 103 can be implemented using various approaches. For example, in one embodiment, image quality weighting subsystem 103 is implemented using a cloud-based approach. In another embodiment, image quality weighting subsystem 103 is implemented across one or more facilities, where each of the components of image quality weighting subsystem 103 are located in different facilities and coupled together using, for example, a network-based connection. In a further embodiment, image quality weighting subsystem 103 is implemented within a single server or computer. In yet another embodiment, image quality weighting subsystem 103 is implemented in software. In another embodiment, image quality weighting subsystem 103 is implemented using a combination of software and hardware.

In one embodiment, in step 202 image quality weighting subsystem 103 first performs decompression of the received image data if necessary. As part of step 202, image quality weighting subsystem 103 either creates a new multimodal image set comprising images from one or more modalities for a patient, and adds the images corresponding to the patient to the multimodal image set; or augments an existing multimodal image set for the patient by adding the images from one or more modalities corresponding to the patient to the multimodal image set.

This multimodal image set is stored in, for example, imaging database 106.

As explained previously, as part of step 202, image quality weighting subsystem 103 may perform one or more image quality weighting operations using the received image data, to obtain corresponding quality metrics such as image quality scores or image quality measures. Parameters used within the one or more image quality weighting operations are combined to determine the quality metrics. Those parameters are, for example:

- Spatial resolution of the images (slice thickness and in-plane): The higher the resolution, the higher the image quality score is likely to be. Image resolution is relative to the modality and slice thickness, therefore resolution may be normalized between modalities by dividing the resolution by the measured volume.
- Signal to noise ratio (SNR): Higher resolution images may have a lower signal to noise ratio, resulting in less grainy images.
- Image contrast: greater contrast may provide improved anatomic detail.
- Image information provided: may include signal averages, flip angles, bandwidths, field of view (FOV), voxel size, good enhancement on a T2-weighted spin echo.
- Absence of artifacts, such as movement artifacts.
- Number of slices (partitions).
- Coverage of the image(s).
- Nearness to edge of structures.
- The number of overlapping images: The higher the number of overlaid or overlapping images, the higher the image quality score is likely to be.
- The degree of match between images: The more overlapping or similar the two images are and the less one image must be distorted to register with the other image, the higher the image quality score is likely to be.
- The number of modalities of images: The higher the number of modalities in the multimodal image set for the patient to which the image corresponds, the higher the image quality score is likely to be.
- The level of training and/or competency of the person who captured the images, which in some embodiments includes one or more scores associated with their competency: The higher the level of training and/or competency, the higher the image quality score is likely to be.
- The institution at which the image capture took place.
- Calibration status and last known calibration date of the subsystem used to acquire the data: Data from calibrated subsystems will receive a higher quality score than data from uncalibrated subsystems. The more recently the calibration of the subsystem, the higher the quality score is likely to be.
- Correlation to supporting additional data: The higher the correlation between image data and supporting additional data, the higher the image quality score is likely to be.

These quality metrics and image data are then stored in imaging database 106, together with the new or updated multimodal image data set. In one embodiment, a new record is either created or an existing record is updated for the patient. In some embodiments, prior to creating a new record or updating an existing record, the quality metrics are compared to one or more thresholds. If the quality metrics do not exceed the one or more thresholds, then in some embodiments, the image data is discarded and not stored in imaging database 106. In other embodiments, the image data for which the quality metrics do not exceed the one or more thresholds is stored in imaging database 106 and designated as lower quality image data.

Once step 202 is completed, in step 203 the image data and multimodal image data set are retrieved by image registration subsystem 104 from imaging database 106 via interconnection 102, so as to perform image registration using quantitative metrics obtained in step 201. Image registration subsystem 104 is coupled to the other components of system 100 via interconnection 102 as shown in FIG. 1.

Image registration subsystem 104 can be implemented using various approaches. As explained previously, the sizes of the image files are in the order of GB or TB. Furthermore, it is likely that the operations necessary to implement image registration are complex. Therefore, as would be appreciated by one of skill in the art, due to the combination of these large image files and the necessity to perform complex operations, image registration is implemented using computer-based solutions. In some embodiments, as explained previously, image registration is facilitated using high-speed computers or processors. For example, in one embodiment, image registration subsystem 104 is implemented using a cloud-based approach. In some embodiments, as explained previously, AI-based techniques are used to perform image registration. In other embodiments, image registration subsystem 104 is implemented across one or more facilities, where each of the components of image registration subsystem 104 are located in different facilities and coupled together using, for example, a network-based connection. In further embodiments, image registration subsystem 104 is implemented within a single server or computer. In yet another embodiment, image registration subsystem 104 is implemented in software. In another embodiment, image registration subsystem 104 is implemented using a combination of software and hardware.

In step 203, as part of the image registration process, image registration subsystem 104 uses the quantitative metrics obtained in step 201 to perform image registration. In one embodiment, multiple images from the same patient, where the images are collected at any point before, during or after treatment, are registered. In one embodiment, the image registration process involves one or more transformation operations. The record corresponding to the patient in imaging database 106 is then updated. In some embodiments, image data which was designated as lower quality image data in step 202 are not utilized in the image registration process.

Once this is complete, in step 204 the voxel quality processing subsystem 105 retrieves the records updated in step 203 from imaging database 106 via interconnection 102 and either creates or updates one or more voxels. Voxel quality processing subsystem 105 is coupled to the other components of system 100 via interconnection 102 as shown in FIG. 1 Voxel quality processing subsystem 105 can be implemented using various approaches. For example, in one embodiment, voxel quality processing subsystem 105 is implemented using a cloud-based approach. In another embodiment, voxel quality processing subsystem 105 is implemented across one or more facilities, where each of the components of voxel quality processing subsystem 105 are located in different facilities and coupled together using, for example, a network-based connection. In a further embodiment, voxel quality processing subsystem 105 is implemented within a single server or computer. In yet another embodiment, voxel quality processing subsystem 105 is implemented in software. In another embodiment, voxel quality processing subsystem 105 is implemented using a combination of software and hardware. Then, in step 204, for the multimodal image set, the voxel quality processing subsystem 105 creates one or more voxels if these voxels have not already been created, or updates a set of voxels corresponding to the multimodal image set. As part of the creation or updating process, the voxel quality processing subsystem determines position information corresponding to the voxel.

In step 205, the voxel quality processing subsystem 105 calculates a voxel quality metric for each voxel using a plurality of parameters. These parameters comprise, for example:
Resolutions of images,
Quantity of images, and
Quantity of imaging modalities.

The calculation of the voxel quality metric for each voxel enables improved diagnosis and medical decision making. It also enables better prediction of the outcomes of treatment programs and comparison of actual and predicted outcomes.

In step 206, the voxel quality processing subsystem 105 assigns the calculated voxel quality metric to the corresponding voxel. Furthermore, as part of step 206, voxel quality processing subsystem 105 uses the patient record to create or update a searchable header. In one embodiment, the searchable header comprises at least one of: a physician, a diagnosis, a treatment, a patient outcome and a medical facility. The searchable header, set of voxels, the position information corresponding to each member of the set of voxels, and the assigned voxel quality metrics are stored within imaging database 106. The creation and updating of a searchable header serves to improve electronic database search and retrieval.

In step 207, the image assembly subsystem 107 retrieves the stored voxels from imaging database 106 via interconnection 102 and assembles a plurality of the stored voxels, each having an associated voxel quality metric, to provide an image of a patient tissue or region with an associated image quality metric. Image assembly subsystem 107 is coupled to the other components of system 100 via interconnection 102 as shown in FIG. 1. Image assembly subsystem 107 can be implemented using various approaches. For example, in one embodiment, image assembly subsystem 107 is implemented using a cloud-based approach. In another embodiment, image assembly subsystem 107 is implemented across one or more facilities, where each of the components of image assembly subsystem 107 are located in different facilities and coupled together using, for example, a network-based connection. In a further embodiment, image assembly subsystem 107 is implemented within a single server or computer. In yet another embodiment, image assembly subsystem 107 is implemented in software. In another embodiment, image assembly subsystem 107 is implemented using a combination of software and hardware. The voxels are assembled into an image using the voxel position information. Thus, at any time a practitioner or institute may acquire an image of a patient corresponding to a point in time or treatment program and be informed of the quality of the image. Once assembly is completed, the image is stored in imaging database 106 by image assembly subsystem 107 using interconnection 102.

Voxel and image quality metrics can provide more accurate conclusions on treatment effectiveness, patient outcome and practitioner performance. For example, a patient undergoes a program comprising multiple treatments performed at different times. At a time corresponding to one of the multiple treatments, the processes outlined above are repeated. In this way, images corresponding to the different times are captured and processed as explained above.

For example, images are captured and processed as described above before, during and after a treatment of a patient. Once this is completed, the images are analyzed to determine the outcome of the treatment and any other diagnoses which may be relevant. The outcome and records corresponding to the treatment are stored in the record corresponding to the patient in imaging database 106. In an additional embodiment, the searchable header as explained above is either created or updated to reflect the outcomes, diagnoses and treatments. In a further embodiment, in the case of multiple treatment steps, the order of treatment steps is also stored and indexed in imaging database 106 as part of the patient record.

The progress of a disease or a condition may be better predicted with these higher quality images. Then, based on these improved predictions, better and more timely treatment decisions may be made. Predicted outcomes may then be compared with actual outcomes to gauge the success or failure of treatment decisions made. Validations of the type and amount of delivered medication are also facilitated using these higher quality images.

Image data sets with corresponding quality metrics can be weighed to formulate better decisions on predictive outcomes and to make a diagnosis of tissue type, such as a tumor type.

These higher quality images may increase the spatial accuracy of an MR image or of an imaging tool, such as a Raman probe. A spectroscopic measurement from a Raman tracked probe or a view from a registered fluorescence microscope may be more accurately positioned within a tissue or in relation to a tumor.

These higher quality images and corresponding information on the quality metric may also be used to better evaluate the effectiveness of addition of treatments, such as alternating electric field therapy, leading edge radiation therapy, focused ultrasound and immunotherapy.

In some embodiments, based on these improved predictions and higher quality images, modifications are made to treatments. In some example embodiments, one or more of the steps in the treatment is changed based on these improved predictions and higher quality images. In other example embodiments, the order of the steps in the treatment is changed based on these improved predictions and higher quality images. In other embodiments, one or more steps are eliminated based on these improved predictions and higher quality images. In some embodiments, treatments are left unchanged.

Although the algorithms described above including those with reference to the foregoing flow charts have been described separately, it should be understood that any two or more of the algorithms disclosed herein can be combined in any combination. Any of the methods, algorithms, implementations, or procedures described herein can include machine-readable instructions for execution by: (a) a processor, (b) a controller, and/or (c) any other suitable processing device. Any algorithm, software, or method disclosed herein can be embodied in software stored on a non-transitory tangible medium such as, for example, a flash memory, a CD-ROM, a floppy disk, a hard drive, a digital versatile disk (DVD), or other memory devices, but persons of ordinary skill in the art will readily appreciate that the entire algorithm and/or parts thereof could alternatively be executed by a device other than a controller and/or embodied in firmware or dedicated hardware in a well-known manner (e.g., it may be implemented by an application specific integrated circuit (ASIC), a programmable logic device (PLD), a field programmable logic device (FPLD), discrete logic, etc.). Also, some or all of the machine-readable instructions represented in any flowchart depicted herein can be implemented manually as opposed to automatically by a controller, processor, or similar computing device or machine. Further, although specific algorithms are described with reference to flowcharts depicted herein, persons of ordinary skill in the art will readily appreciate that many other methods of implementing the example machine readable instructions may alternatively be used. For example, the order of execution of the blocks may be changed, and/or some of the blocks described may be changed, eliminated, or combined.

It should be noted that the algorithms are illustrated and discussed herein as having various modules which perform particular functions and interact with one another. It should be understood that these modules are merely segregated based on their function for the sake of description and represent computer hardware and/or executable software code which is stored on a computer-readable medium for execution on appropriate computing hardware. The various functions of the different modules and units can be combined or segregated as hardware and/or software stored on a non-transitory computer-readable medium as above as modules in any manner, and can be used separately or in combination.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of an invention as defined in the appended claims.

What is claimed is:

1. A computer-implemented method to store and analyze clinical imaging data for a treatment program comprising:
    obtaining two or more images of a patient from two or more modalities;
    registering the images to provide a multi-modal image set;
    determining a position information of a voxel in the multi-modal image set;
    calculating a quality metric for the voxel of the multi-modal image set;
    assigning the quality metric to the voxel; and
    storing the voxel, the voxel position information, the quality metric and at least one searchable header as imaging data in a memory of a computing device; and
    modifying or maintaining the treatment program based on the imaging data;
    wherein the quality metric for the voxel is calculated from parameters comprising a resolution of the images, a quantity of the images and a quantity of the imaging modalities.

2. The method of claim 1, wherein the registering uses quantitative metrics from the images.

3. The method of claim 1, wherein the images are obtained at different times.

4. The method of claim 3, wherein the different times are before a treatment, during the treatment and after the treatment of the patient.

5. The method of claim 4, further comprising analyzing the imaging data to determine a treatment outcome and storing the treatment and the outcome with the imaging data.

6. The method of claim 5, wherein the treatment comprises more than one treatment step and storing the treatment includes storing the order of treatment steps.

7. The method of claim 1, wherein the two or more images include a biopsy image.

8. The method of claim 1, wherein the searchable header comprises at least one of: a physician, a diagnosis, a treatment, a patient outcome and a medical facility.

9. The method of claim 1, further comprising assembling an image associated with a quality metric by combining a plurality of the stored voxels.

10. A system for storing and analyzing clinical imaging data for a treatment program, comprising:
    a memory; and
    a processor interconnected with the memory, the processor configured to:
        obtain two or more images from two or more modalities;
        store the images in the memory;
        register the images to provide a multi-modal image set;
        store the multi-modal image set in the memory;
        calculate a quality metric for a voxel in the multi-modal image set;
        store the voxel quality metric with the multi-modal image set in the memory; and
        modify or maintain the treatment program based on the calculated quality metric;
    wherein the quality metric for the voxel is calculated from parameters comprising a resolution of the images, a quantity of the images and a quantity of the imaging modalities.

11. The system of claim 10, further comprising a searchable database in communication with the processor to store the multi-modal image set and voxel quality metric.

* * * * *